US005320600A

United States Patent [19]

Lambert

[11] Patent Number: 5,320,600

[45] Date of Patent: Jun. 14, 1994

[54] PLURAL CONTENT CONTAINER FOR SIMULTANEOUS EJECTION

[76] Inventor: Wm. S. Lambert, 52 Tokalon, Metairie, La. 70001

[21] Appl. No.: 77,429

[22] Filed: Jun. 14, 1993

[51] Int. Cl.[5] ............ A61M 37/00

[52] U.S. Cl. ............ 604/47; 604/212; 604/272; 128/743

[58] Field of Search ............ 604/46, 47, 173, 181, 604/187, 212, 216, 239, 272; 128/743

[56] References Cited

U.S. PATENT DOCUMENTS 5,076,282 12/1991 Fishman et al. ............ 128/743
5,097,810 3/1992 Fishman et al. ............ 128/743
5,099,857 3/1992 Baldo et al. ............ 128/743

FOREIGN PATENT DOCUMENTS 0046105 8/1962 Poland .

*Primary Examiner*—C. Fred Rosenbaum
*Assistant Examiner*—Connie Maglione

[57] ABSTRACT

A device to effect simultaneous, en masse compressive-ejection of the content of plural, enveloped-ejectant containment-pods mounted therewithin the device.

3 Claims, 4 Drawing Sheets

PLURAL CONTENT CONTAINER FOR SIMULTANEOUS EJECTION

BACKGROUND OF THE INVENTION

1. Field of the Invention

Modal application of maneuverable cam lobe action to transferrably effect compressive content movement.

2. Description of the Related Art

In varied forms, per se cam lobe action has been utilized indefinitely. The principal of the peristalic pump, or a common tube of toothpaste, offer representative examples, in the singular, of the effect. Applicant is uninformed of specific prior implementation for such particular application hereinafter disclosed for the multiple-compressive, cam lobe conductive ejection of container content involving multiple reservoir expulsion, exitable through outlets includable of complementary conductive tubing.

BRIEF SUMMARY OF THE INVENTION

The novelty of the instant is most clearly and definitively disclosed per the following descriptive example of a specific utilization.

Inherent with standard subdermal tissue, as well as surface skin perforation, is accidental scratch/stick (AIDS) exposure. Instant will recoup immeasurable expensive healthcare clocktime now wasted by current procedures. The object realized in this utilization of the instant is the reduction of patient discomfort, as limited to no more than those minimal seconds for the implantation of a selected plurality in the standard aggregate of injectants. Custom mounted individually by hand, or factory standard aggregate-loads, in single plate strips of, say 5 to 10 appropriately-spaced injectant pod envelopes in conjunctive tandem. Implementation is extensible per side-to-side, teamed attachment per adhesive side-pads, or transversely securable simply by drugstore adhesive tape. An expandable plurality of individual hypodermic ejector pods so mountable in-tandem upon an (optionally epidermis-adherable) plate strip, and actuatable per contactive compressive transversal thereover by the complementary actuator lobes formed in the separate, housing cover shell, as slidably interlock-able (to effect simultaneous, en masse, subdermal tissue infusion).

BRIEF DESCRIPTION OF THE DRAWING FIGURES

FIG. 1 is a sequential end view depiction of simultaneous hypodermic injection of aggregated injectants. The operation of the components of the device as accommodative of skin surface or tissue implantation:

1A—poses assembly of the instant, a peripherally sealable, injectant-chargable, reservoir pod, dischargeable through its sterility-assured, centrically suspended, formed hypodermic cannula—mounted (custom hand or factory mass) onto the topside of pod-mounting plate strip carrier, and positioned thereover a punched ejection aperture (see FIG. 2B). Pod composite is held fast there by the combination of: wedging-in between pod plate strip slide-rails, the retentive pressure of the aperture remnant tab (see FIGS. 1B and 2B), as well as optional, coincidental contactive attachment to the partially exposed (see FIG. 2C) layer of strip-able adhesive, bottom side of the pod plate, through the punched aperture. The adhesive is preserved there by a peel-away guard film. The actuator housing cover can be compressibly snap-latched tongue and groove, over and along the lateral, slide-rail periphery of pod plate, and then linearly slide-able there along (see FIG. 2C).

1B—a cross section end view through device at the center of a pre-actuatable ejector pod. The optional layer of adhesive is shown partially "blocked-out" at ejection aperture (see FIG. 2C), also allowing contact therewith. Incorporation of aperture tab remnant into function is as indicated. (Note example representative of subdermally injective cannula. Pod is down-sizable to accommodate an inoculator sharp)

1C—passage of cam lobe over pod center (see FIG. 2D) collapsibly, compressibly, effects maximum inoculant saturation of immedia epidermis, and resistive of pressurized, peripheral "blow-by" leakage. Note, for maximal deposit, the "shoveling-open", spreading-open effect(arrows) of the inner circumference of the tissue incision per the tapered, beveled free-end of cannula.

1D—spent device is shown as stripped from epidermis and inverted.

1E—empty housing prior to protective disposal preparation snap-in or slide-in re-insertion of spent pod plate, including contaminated sharps 1F—peel-out, spring-back(arrows) peripheral housing free edges are so receivable of slide-in or snap-in re-insertion of spent pod plate.

1G—inverted housing cover interlocks contaminated sharps with bottom side of pod plate with adhesive layer, against upper interior surface of housing cover for so-forced, and thus, protectively adhered for(broad arrow) safe disposal.

FIG. 2 depicts operational phasing of device structural elements:

2A—a cut-away view of a typical section shows housing, including its actuator cam lobe, as slide-ably and peripherally conjoined(tongue and groove) to the pod mounting plate, indicating an optional layer of strip-a semi-adhesive on its bottom side—as preserved by a peel-able guard film 2B—shows pod mounting plate, with pre-punched, aperture remnant tab, which coincidentally and compressively positions pod over aperture, as aided by: tab crimped corners, pod wedging-in between the spreadable pod plate slide-rails, and concurrent adherence to aperture-exposed adhesive layer.

2C—cut-away view shows housing cover, slide-able over punched (and optionally corrugated)aperture remnant tab as toward compressive actuation of ejector pods therebeneath.

2D—per positioning of actuator cam-lobe fully over tab pod, total compressed diffusion of injectant or inoculant has occurred. Discharge thus consummated, spent article to be prepared for, and safely disposed.

DRAWING REFERENCE NUMERALS

10—ejector pod reservoir ensemble, including cannula

12—lid-seal bulkhead portion of pod ensemble 10

13—angle-sharpened cannula including exit flow ports

14—bevel shovel inoculator with skewed-angle, serrated, micro-sharp, thin cutting edge—including flow ports 18—resilient telescopically collapsible reservoir sidewall of pod 10

30—pod mounting base plate strip, including punched aperture tab, as retainably receivable of individual pods, fixedly positionable over apertures, wedged in by plate sidewalls and bound to exposed adhesive 31—optional sharp mini-corrugations minimize slide frictional contact 32—strip-able semi-adhesive layer(optional), bottom side of plate contacts injection site 34—aperture tab remnant, as punched 35 from base plate strip 30

35—aperture as punched through and from plate strip 30

36—corner tips of tab 34 are crimp-able over pod periphery

39—guard cover film is protectively preservative of adhesive 32

50—slidable housing shell cover with actuator lobes so-formed therein, including before-use and after-use, M/F spring-latch interlock 30/50

51—arrow suggesting 180 degree inversion of 50 for disposal preparation

52—maximally expulsive, actuator cam lobe of housing 50

53—arrows 53 show peel-back/spring-back latching 30/50 over lateral periphery of the spent pod plate strip 30 for protective re-insertion for disposal 54—pod plate 30 is forcible against interior upper surface of housing 50, to lock in protection of contaminated sharps 57—optional sharp corrugations increase linear planar reinforcement of 50.

DETAILED DESCRIPTION OF THE INVENTION

Figure 1A:
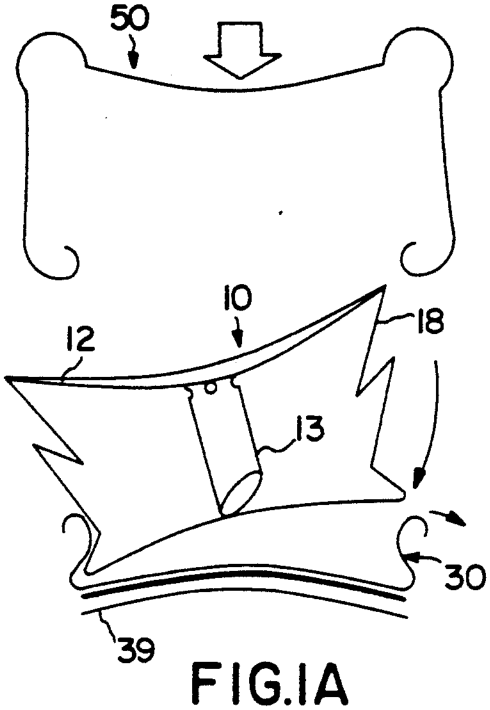

The preferred embodiment of the invention includes a first portion comprising an appropriately dimensioned, pod mountable, semi-resilient plate strip 30 upon which upper surface is fixedly secured a tandem plurality of ejector pods 10, each positioned accessibly over identically spaced, pre-punched ejection apertures 35. The bottom side of plate strip 30 is peel-ably adhereable to epidermal surface, in toto, per optional contiguous attachment of a free layer of semi-adhesive 32, adherable to the said bottom surface of the plate strip. An outer, removable guard film 39 preserves such adhesive 32. Pods are retained in position per: inherent compression of aperture tab 34 with optional, retentive, crimped corner tips 36, wedging effect of plate 30 slide-rails, and coincidental adherence to that portion of adhesive 32 partially exposed within ejection aperture 35.

The ejector pods 10 are burst-resistant ejectant-reservoirs. They are each made of a resilient, axially compressible, hermetically sealed, cylindrical pod envelope with a flat upper endwall and a contraposed, self penetratable lower endwall. The endwalls are spaced apart per the static volume pressure of an injectant loaded there between and sealably joined by a resilient thin-film sidewall. Contained centrically suspended therewithin is a sterility-assured, hypodermic cannula 13 for subdermal tissue implantation, including a strongback or preferred bulkhead and lid 12 to anchor said cannula 13. For allergy testing, the preferred cannula is a which sharply fluted, strengthening, incision-lengthening, linearly corrugated cannula 14, having strategic feed flow porting in one end thereof, which terminates in an opposite end with an inwardly-tapering, beveled, angle-skewed, serrated cutting edge—all, to facilitate penetration, while effecting a "shoveling-enlargement" of tissue-access incision exposure. A 15% gap in the circumference of its cutting edge precludes a tissue "plug" extraction on strip-off removal of spent device.

In lieu of wasting the excess material per the punched aperture tab 34, the same is coincidentally utilized to facilitate smooth, trans-passage of the actuator cam lobe 52 over the center of the pod 10.

Plate strip 30 is complementarily interlocked (30/50) at its lateral periphery by compressive latching or interlocking to the shell cover housing 50. The actuator cam lobes 52 of the housing 50 are spaced complementary of the pod 10 centers. The housing 50 cover shell slidingly traverses linearly over pod plate strip 30, its actuator cam lobes 52 of housing 50 compressibly effecting simultaneous, collective, expulsive dissemination of the total content of all the pods into the epidermis and/or deeper.

Content ejection rate can be slowed, either by deceleration of slide-action and/or, per pre-insertion of an open-celled sponge media insert within each containment pod.

Slide-rail contactive friction can be reduced by formed mini-corrugations 31 on the rail surface and/or, further per an oleic additive into the poly-plastic formulation of housing 50.

Figure 1B:
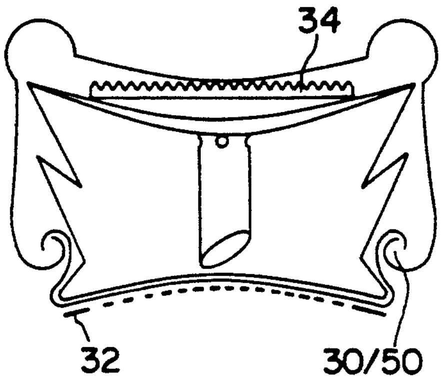

Minimal compositional adjustments, including (see FIG. 1B) upsizing for interposition of an appropriate, deeper-injecting hypodermic needle in the place of the inoculation cannula will transmutably render effective an embodiment employable for en masse hypodermic injection as for say, military movements (i.e., Persian Gulf), human disasters (i.e., flood, earthquake, government aid program), etc. Such a medically standard, aggregate-pack, presumably to include such medicaments as tetanus, penicillin, vitamin boosters, antidote packs for poisons, etc. Of most critical importance is the simplistic functional utilization access by those of absolute minimal physical ability—one such human to so "inject" another, even the Blind. Professional Health-Care personnel attention is thus freed for more complex human-need assistance.

One mechanical operation of the device is most efficiently disclosed per an actual allergy testing embodiment implementation scenario as follows:

Selected individual inoculator pods 10 are mounted over the fixedly spaced, punched apertures 35. The pods are lightly wedged between the peripheral, spreadable slide-rails of the plate strip 30, and tucked compressively beneath aperture tabs 34 (while coincidentally adhering to the optional adhesive layer 32, as partially exposed within ejection aperture 35).

The peripheral slide-rails of the base plate strip 30 are then compressively interlocked with the formed linear shell housing 50. A guard film 39 is peel-able to expose an optional semi-mucilaginous layer 32 for strip-able contactive adherence of the bottom-side of the device to say, the alcohol-sponged vertical quarterpoint of a patients back.

Figure 1C:
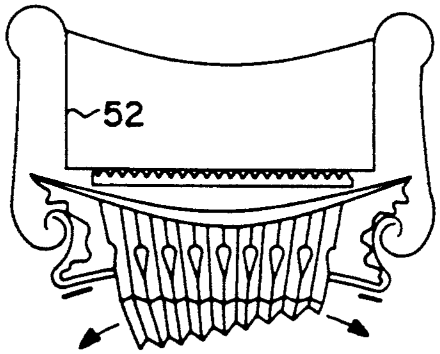
Figure 1D:
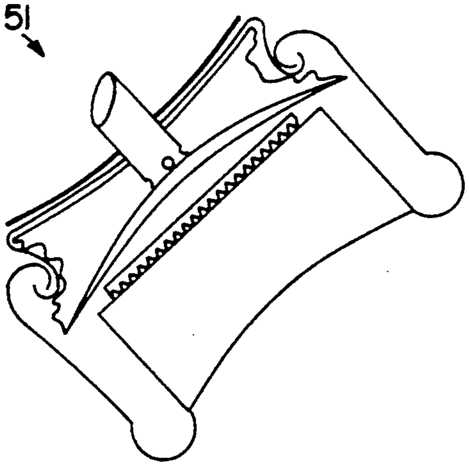
Figure 1E:
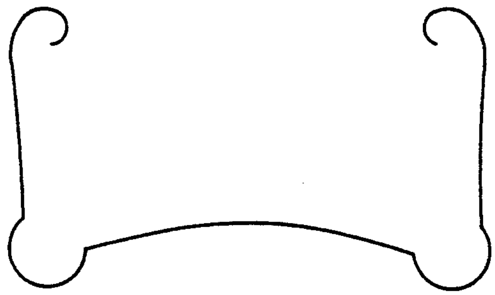
Figure 1F:
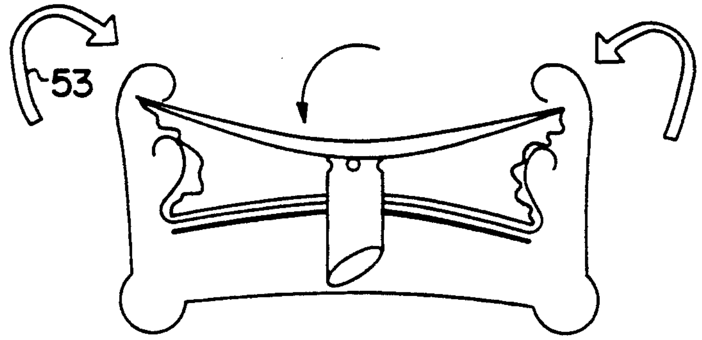
Figure 1G:
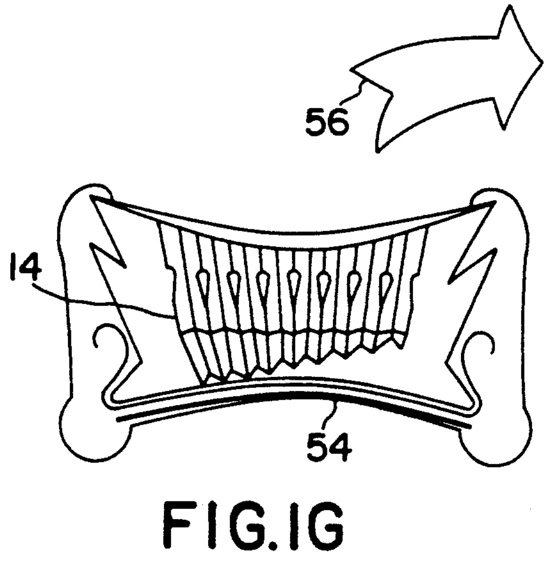
Figure 2A:
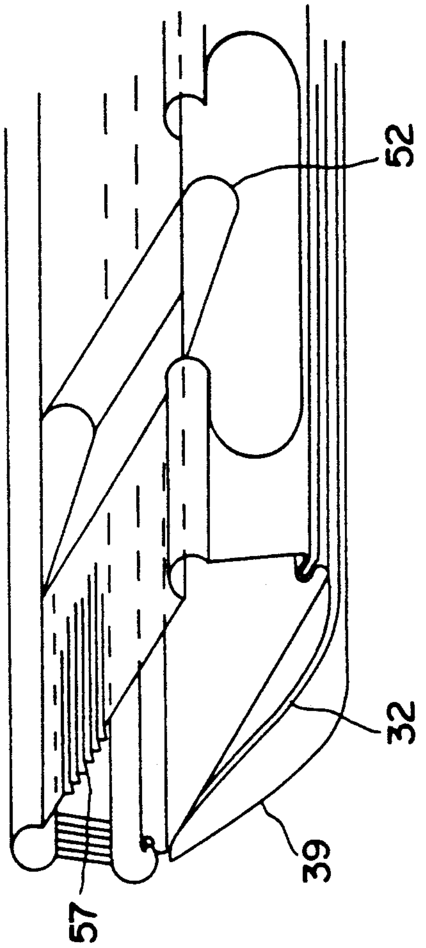
Figure 2C:
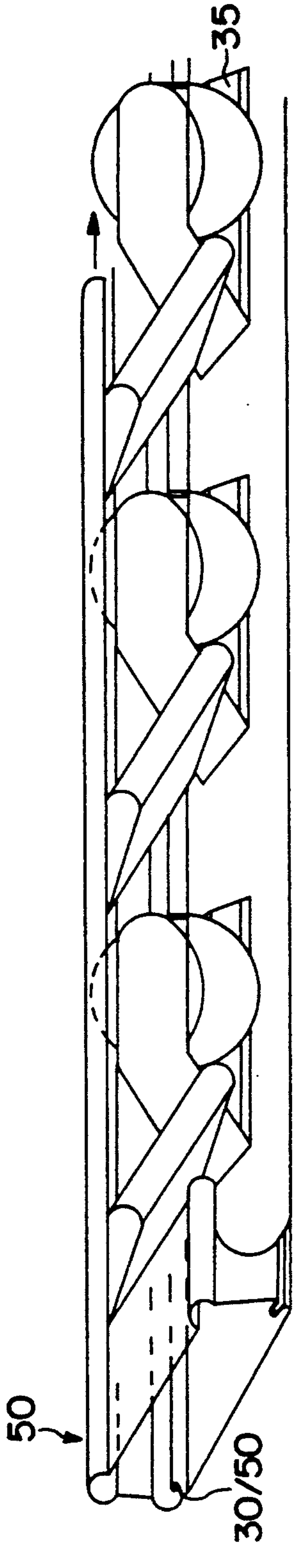
Figure 2B:
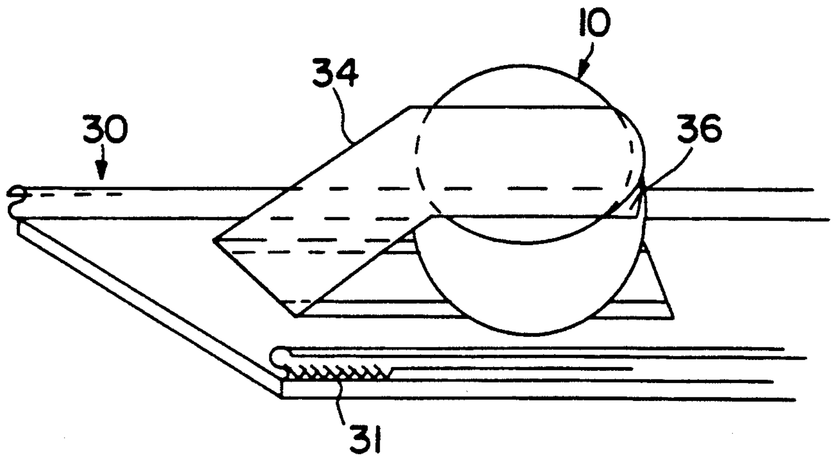
Figure 2D:
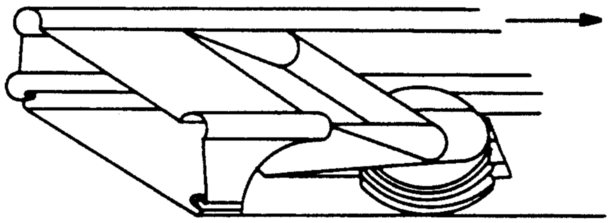

In one rapid motion, the housing actuator 50 is linearly slid so that the actuator cam lobes 52 formed in the housing 50 lid portion are passed transversely and compressibly over the aperture tab 34—and thus pod 10 center—to effect hypodermic dissemination of the specimen into patients epidermis. The micro sharp, (optionally silicone and/or Teflon-coated) cannula 14 is sharply corrugated for strength and maximum incision exposure. The skewed angle of the serrated cutting edge facilitates simultaneous penetration (FIG. 1C) through both pod 10 bottom and epidermis therebeneath. Minimally-thin pod envelope is formulated to centripetally, molecularly contract sealingly around the perimeter of the cannula passing therethru. The bevel of the cannula tip tends toward an external, circumferential, forced contactive-sealing to resist "blow-by" leakage while "shoveling-open" the incision inner perimeter to further facilitate infusion thereof. Some fifteen percent of the cutting edge circle is absented to preclude any tendency to extract a tissue "plug" during strip-off of device.

Penetrative, collective, total en masse inoculation is effected and device is strip-ably removable in less than thirty seconds. Consecutive inoculant identification numbers can be (alcohol-soluble) pre-inked onto bottom of the optional adhesive layer to be coincidentally and clearly transferred adjacent each epidermal inoculation site to facilitate accurate observation and recordation. A consummative alcohol sponge bath is applied to cleanse overall inoculation site.

As sized for injection, or inoculation, pod plate 30 with mounted contaminated sharps is removable from housing 50, inverted 180 degrees, and snap-latchably (30/50/12) re-installed back into housing 50 with adhesive 32 (if desired) on bottomside of plate 30 forced hard against inside of housing 50 lid. There-fixed, contaminated sharps are protectively safeguarded for disposal. Preferred is the in to composition of biodegradable poly-plastic—also totally incineratable.

Intended exclusively to minimize patient discomfort, the total duration of mechanical tissue-entry-to-retraction is absolutely assured to consume less than some thirty seconds. A textbook example of a decades-old patient ordeal of suffering lessened or eliminated per the simplistic efficiency of this brand-new fabricated device. Minimization of such sensory testing discomfort is most acutely pertinent to the injectee.

I claim:

1. A composite device for simultaneous, en-masse cam lobe actuation of the contents of a plurality of individually mounted injectant containment pod envelopes, the device comprising:

a plurality of pods each consisting of a hermetically sealable, self-contained pod unit made of a reconformably resilient, comprehensive envelope having an upper and a lower endwall with an injectant there between, a resilient common film sidewall joining the upper endwall to the lower endwall, and a cannula centrically suspended within the pod unit, the cannula of which comprises an upper butt-end serving as the upper endwall of the pod, a sharpened end opposite the upper butt-end and feed inlet perforations at the upper butt-end; and a flexible carrier-base plate strip having a plurality of ejection apertures punched there through, each with an individual pod fixed thereto, and an invertible, slidable cover shell housing, complementarily and slidably engaged to the carrier-base plate by means of lateral, snap-in tongue and groove interlocks, having a plurality of intervally spaced actuator cam lobes extending perpendicularly down therefrom to compressibly pass over and thus actuate simultaneous injectant content voiding of the pods mounted correspondingly to the cam lobes upon sliding the cover shell relative to the base plate, whereby upon depression of the upper end walls of the pods toward the lower endwalls, the cannulas of each pod centrically penetrate the lower endwalls for total conductive evacuation of the pod contents, employable as an epidermal inoculator or for deeper subdermal tissue implantation as per appropriate proportioning and cannula selection.

2. The device of claim 1 as applicable to skin allergy testing, further comprising an appropriately formed inoculative cannula, reinforceable per longitudinal corrugation circumferentially about its shaft, and having uppermost strategic feed porting, and a lowermost free end skewed cutting edge, peripherally beveled inwardly, and serrated to facilitate simultaneous, ejective penetration thru discharge endwall to saturate that skin.

3. The device of claim 1, further comprising a means for contactive securement to a planar surface, object, or body part epidermis, having a free layer of a semi-adhesive attachable to the bottom side surface of said plate strip and preservable there per a peel-able guard film thereover.

* * * * *